United States Patent
Kust et al.

(10) Patent No.: US 10,206,731 B2
(45) Date of Patent: Feb. 19, 2019

(54) TORQUE-LIMITING SCREWDRIVERS

(71) Applicant: Pro-Dex, Inc., Irvine, CA (US)

(72) Inventors: Richard Kust, Lake Forest, CA (US); John Joseph Desrosiers, San Clemente, CA (US); Francis James Steinmetz, Whittier, CA (US); Dung Ma, Anaheim, CA (US); Siddharth Desai, Ladera Ranch, CA (US)

(73) Assignee: Pro-Dex, Inc., Irvine, CA (US)

( * ) Notice: Subject to any disclaimer, the term of this patent is extended or adjusted under 35 U.S.C. 154(b) by 546 days.

(21) Appl. No.: 15/044,396

(22) Filed: Feb. 16, 2016

(65) Prior Publication Data
US 2016/0256213 A1 Sep. 8, 2016

Related U.S. Application Data

(62) Division of application No. 14/332,964, filed on Jul. 16, 2014, now Pat. No. 9,265,551.
(Continued)

(51) Int. Cl.
*A61B 17/58* (2006.01)
*A61B 17/60* (2006.01)
(Continued)

(52) U.S. Cl.
CPC ........ *A61B 17/8875* (2013.01); *B25B 21/002* (2013.01); *B25B 23/14* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 2,414,882 | A | 1/1947 | Longfellow |
| 2,979,089 | A | 4/1961 | Piesker |

(Continued)

FOREIGN PATENT DOCUMENTS

| | | |
|---|---|---|
| DE | 19620782 A1 | 12/1996 |
| JP | H06-210575 A | 8/1994 |

(Continued)

OTHER PUBLICATIONS

Hatcher, "Evaluation of the iQ™ Intelligent System for Rapid Screw Insertion," undated but believed to be publicly available at least as early as Dec. 2012 (e.g., via http://pharma-gate.net/wp-content/uploads/ 2012/12/1.pdf).

(Continued)

*Primary Examiner* — Sameh Boles
(74) *Attorney, Agent, or Firm* — Knobbe, Martens, Olson & Bear, LLP

(57) ABSTRACT

Various torque-limiting screwdrivers, systems, and methods are disclosed. The screwdriver can include a body supporting a motor configured to rotate a screw engaged with the screwdriver. The screwdriver can include a controller configured to implement torque-limiting functionality, such as by monitoring the amount of torque applied to the screw and reducing or stopping rotation of the screw when certain torque-limiting criteria are met. Some embodiments include a threshold point, after which the torque-limiting functionality can be engaged. Some embodiments include a slow-down point, after which the rotational speed of the screw is reduced.

22 Claims, 10 Drawing Sheets

Related U.S. Application Data

(60) Provisional application No. 61/940,197, filed on Feb. 14, 2014, provisional application No. 61/937,346, filed on Feb. 7, 2014, provisional application No. 61/872,427, filed on Aug. 30, 2013, provisional application No. 61/856,557, filed on Jul. 19, 2013.

(51) Int. Cl.
*A61F 2/00* (2006.01)
*A61B 17/88* (2006.01)
*B25B 21/00* (2006.01)
*B25B 23/147* (2006.01)
*B25B 23/14* (2006.01)
*A61B 90/00* (2016.01)
*A61B 17/00* (2006.01)

(52) U.S. Cl.
CPC .. *B25B 23/147* (2013.01); *A61B 2017/00075* (2013.01); *A61B 2090/031* (2016.02)

(56) References Cited

U.S. PATENT DOCUMENTS

| | | |
|---|---|---|
| 3,120,845 A | 2/1964 | Horner |
| 3,578,872 A | 5/1971 | McBurnie |
| 3,926,264 A | 12/1975 | Bardwell et al. |
| 3,962,910 A | 6/1976 | Spyridakis et al. |
| 3,973,434 A | 8/1976 | Smith |
| 3,974,685 A | 8/1976 | Walker |
| 3,974,883 A | 8/1976 | Sigmund |
| 3,982,419 A | 9/1976 | Boys |
| 4,008,772 A | 2/1977 | Boys |
| 4,008,773 A | 2/1977 | Wallace et al. |
| 4,023,406 A | 5/1977 | Benz, Jr. |
| 4,078,589 A | 3/1978 | Miller |
| 4,081,037 A | 3/1978 | Jonsson |
| 4,095,325 A | 6/1978 | Hashimoto et al. |
| 4,102,182 A | 7/1978 | Brown et al. |
| 4,104,778 A | 8/1978 | Vliet |
| 4,104,780 A | 8/1978 | Sigmund |
| 4,106,176 A | 8/1978 | Rice et al. |
| 4,110,829 A | 8/1978 | Boys |
| 4,163,310 A | 8/1979 | Sigmund |
| 4,179,786 A | 12/1979 | Eshghy |
| 4,233,721 A | 11/1980 | Eshghy |
| 4,244,213 A | 1/1981 | Marcinkiewicz |
| 4,249,117 A | 2/1981 | Leukhardt et al. |
| 4,267,914 A | 5/1981 | Saar |
| 4,273,198 A | 6/1981 | Doniwa |
| 4,292,571 A | 9/1981 | Cuneo |
| 4,344,216 A | 8/1982 | Finkelston |
| 4,359,906 A | 11/1982 | Cordey |
| 4,361,945 A | 12/1982 | Eshghy |
| 4,375,120 A | 3/1983 | Sigmund |
| 4,375,121 A | 3/1983 | Sigmund |
| 4,375,122 A | 3/1983 | Sigmund |
| 4,375,123 A | 3/1983 | Ney |
| 4,426,588 A | 1/1984 | Weilenmann |
| RE31,569 E | 5/1984 | Eshghy |
| 4,450,727 A | 5/1984 | Reinholm et al. |
| 4,562,389 A | 12/1985 | Jundt et al. |
| 4,684,922 A | 8/1987 | Minogue |
| 4,705,038 A | 11/1987 | Sjostrom et al. |
| 4,721,169 A | 1/1988 | Nagasawa et al. |
| 4,830,549 A | 5/1989 | Neumaier et al. |
| 4,894,767 A | 1/1990 | Doniwa |
| 4,908,926 A | 3/1990 | Takeshima et al. |
| 4,995,877 A | 2/1991 | Ams et al. |
| 5,014,793 A | 5/1991 | Germanton |
| 5,038,084 A | 8/1991 | Wing |
| 5,061,885 A | 10/1991 | Fukuhara |
| 5,131,130 A | 7/1992 | Eshghy |
| 5,152,046 A | 10/1992 | Abe |
| 5,154,242 A | 10/1992 | Soshin et al. |
| 5,155,421 A | 10/1992 | Hansson |
| 5,160,978 A | 11/1992 | Faville |
| 5,207,697 A | 5/1993 | Carusillo et al. |
| 5,284,217 A | 2/1994 | Eshghy |
| RE34,556 E | 3/1994 | Sjostrom et al. |
| 5,315,501 A | 5/1994 | Whitehouse |
| 5,337,638 A | 8/1994 | Coss |
| 5,382,251 A | 1/1995 | Hood et al. |
| 5,404,643 A | 4/1995 | Rice |
| 5,410,229 A | 4/1995 | Sebastian et al. |
| 5,440,215 A | 8/1995 | Gilmore |
| 5,496,330 A | 3/1996 | Bates et al. |
| 5,538,423 A | 7/1996 | Coss et al. |
| 5,543,695 A | 8/1996 | Culp et al. |
| 5,563,482 A | 10/1996 | Shaw et al. |
| 5,584,619 A | 12/1996 | Guzzella |
| 5,591,919 A | 1/1997 | Hathaway et al. |
| 5,626,474 A | 5/1997 | Kukla et al. |
| 5,632,759 A | 5/1997 | Rexroth |
| 5,637,968 A | 6/1997 | Kainec et al. |
| 5,689,159 A | 11/1997 | Culp et al. |
| 5,725,533 A | 3/1998 | Carlsson |
| 5,731,673 A | 3/1998 | Gilmore |
| 5,754,019 A | 5/1998 | Walz |
| 5,810,821 A | 9/1998 | Vandewalle |
| 5,868,746 A | 2/1999 | Sarver et al. |
| 5,890,405 A | 4/1999 | Becker |
| 5,898,112 A | 4/1999 | Dawood |
| 5,904,689 A | 5/1999 | Jonjic |
| 5,927,976 A | 7/1999 | Wu |
| 5,980,248 A | 11/1999 | Kusakabe et al. |
| 5,993,454 A | 11/1999 | Longo |
| 6,022,352 A | 2/2000 | Vandewalle |
| 6,110,174 A | 8/2000 | Nichter |
| 6,132,435 A | 10/2000 | Young |
| 6,162,053 A | 12/2000 | Hollander |
| 6,171,312 B1 | 1/2001 | Beaty |
| 6,179,841 B1 | 1/2001 | Jackson |
| 6,197,065 B1 | 3/2001 | Martin et al. |
| 6,211,636 B1 | 4/2001 | Matsubara et al. |
| 6,257,351 B1 | 7/2001 | Ark et al. |
| 6,280,476 B1 | 8/2001 | Metzger et al. |
| RE37,358 E | 9/2001 | Del Rio et al. |
| 6,329,778 B1 | 12/2001 | Culp et al. |
| 6,378,623 B2 | 4/2002 | Kawarai |
| 6,402,757 B1 | 6/2002 | Moore, III et al. |
| 6,471,707 B1 | 10/2002 | Miller et al. |
| 6,479,958 B1 | 11/2002 | Thompson et al. |
| 6,500,208 B1 | 12/2002 | Metzger et al. |
| 6,508,841 B2 | 1/2003 | Martin et al. |
| 6,516,896 B1 | 2/2003 | Bookshar et al. |
| 6,537,274 B1 | 3/2003 | Katz |
| 6,547,565 B1 | 4/2003 | Dawood et al. |
| 6,569,186 B1 | 5/2003 | Winters et al. |
| 6,607,385 B1 | 8/2003 | Sevcik et al. |
| 6,616,446 B1 | 9/2003 | Schmid |
| 6,629,778 B1 | 10/2003 | Enderle et al. |
| 6,656,184 B1 | 12/2003 | White et al. |
| 6,676,665 B2 | 1/2004 | Foley et al. |
| 6,680,595 B2 | 1/2004 | Ito |
| 6,700,341 B2 | 3/2004 | Schaer et al. |
| 6,712,855 B2 | 3/2004 | Martin et al. |
| 6,723,099 B1 | 4/2004 | Goshert |
| 6,780,175 B1 | 8/2004 | Sachdeva et al. |
| 6,916,340 B2 | 7/2005 | Metzger et al. |
| 6,923,813 B2 | 8/2005 | Phillips et al. |
| 6,954,682 B2 | 10/2005 | Makimae et al. |
| 6,981,976 B1 | 1/2006 | Schoenefeld |
| 7,062,979 B2 | 6/2006 | Day et al. |
| 7,091,683 B1 * | 8/2006 | Smith ............... A61B 17/8875 173/176 |
| 7,141,073 B2 | 11/2006 | May et al. |
| 7,234,536 B2 | 6/2007 | Scholl et al. |
| 7,235,940 B2 | 6/2007 | Bosch et al. |
| 7,250,055 B1 | 7/2007 | Vanderwalle |
| 7,255,703 B2 | 8/2007 | Mujwid et al. |
| 7,306,607 B2 | 12/2007 | Metzger |
| 7,331,406 B2 | 2/2008 | Wottreng, Jr. et al. |
| 7,335,207 B1 | 2/2008 | Smith |

(56) References Cited

U.S. PATENT DOCUMENTS

| | | |
|---|---|---|
| 7,338,286 B2 | 3/2008 | Porter et al. |
| 7,344,376 B2 | 3/2008 | Beaty et al. |
| 7,398,700 B2 | 7/2008 | Makimae et al. |
| 7,400,106 B2 | 7/2008 | DeCicco et al. |
| 7,431,682 B2 | 10/2008 | Zeiler et al. |
| 7,435,085 B2 | 10/2008 | Gugel et al. |
| 7,481,832 B1 | 1/2009 | Meridew et al. |
| 7,484,959 B2 | 2/2009 | Porter et al. |
| 7,488,323 B2 | 2/2009 | Bacastow et al. |
| 7,507,231 B2 | 3/2009 | Schmieding et al. |
| 7,604,636 B1 | 10/2009 | Walters et al. |
| 7,713,285 B1 | 5/2010 | Stone et al. |
| 7,722,678 B2 | 5/2010 | Brown et al. |
| 7,727,282 B2 | 6/2010 | Slone et al. |
| 7,740,425 B2 | 6/2010 | Zeiler et al. |
| 7,770,658 B2 | 8/2010 | Ito et al. |
| 7,823,465 B2 | 11/2010 | Makimae et al. |
| 7,839,112 B2 | 11/2010 | Wei |
| 7,849,766 B2 | 12/2010 | Sharifi-Mehr et al. |
| 7,850,452 B2 | 12/2010 | Suttin et al. |
| 7,881,806 B2 | 2/2011 | Horrigan et al. |
| 7,887,559 B2 | 2/2011 | Deng et al. |
| 7,896,923 B2 | 3/2011 | Blackwell et al. |
| 7,936,140 B2 | 5/2011 | Wei |
| 7,955,334 B2 | 6/2011 | Steiner et al. |
| 8,012,215 B2 | 9/2011 | Metzger et al. |
| 8,025,106 B2 | 9/2011 | Schmidt |
| 8,028,608 B2 | 10/2011 | Sixto, Jr. et al. |
| 8,035,487 B2 | 10/2011 | Malackowski |
| 8,038,702 B2 | 10/2011 | Yuan et al. |
| 8,048,115 B2 | 11/2011 | Winslow et al. |
| 8,057,538 B2 | 11/2011 | Bergin et al. |
| 8,074,334 B2 | 12/2011 | Tharp et al. |
| 8,083,596 B1 | 12/2011 | Silver et al. |
| 8,087,935 B2 | 1/2012 | Beaty et al. |
| 8,103,358 B2 | 1/2012 | Sommer et al. |
| 8,136,431 B2 | 3/2012 | Wengreen |
| 8,147,498 B2 | 4/2012 | Schlueter et al. |
| 8,161,613 B2 | 4/2012 | Schuele et al. |
| 8,172,004 B2 | 5/2012 | Ho |
| 8,182,539 B2 | 5/2012 | Tyber et al. |
| 8,276,487 B2 | 10/2012 | Wengreen et al. |
| 8,286,723 B2 | 10/2012 | Puzio et al. |
| 8,322,456 B2 | 12/2012 | Pozgay et al. |
| 8,347,768 B2 | 1/2013 | Witte |
| 8,372,085 B2 | 2/2013 | Prager et al. |
| 8,425,521 B2 | 4/2013 | Cremer et al. |
| 8,463,421 B2 | 6/2013 | Brett et al. |
| 8,485,075 B1 | 7/2013 | Gauthier et al. |
| 8,523,845 B2 | 9/2013 | Ippisch |
| 8,529,567 B2 | 9/2013 | Garcia et al. |
| 9,265,551 B2 | 2/2016 | Kust et al. |
| 9,585,677 B2 | 3/2017 | Garcia et al. |
| 2002/0146663 A1 | 10/2002 | Nakanishi et al. |
| 2003/0093103 A1 | 5/2003 | Malackowski et al. |
| 2003/0121685 A1 | 7/2003 | Yamamoto |
| 2003/0173096 A1 | 9/2003 | Setton et al. |
| 2005/0096684 A1 | 5/2005 | Farrow et al. |
| 2005/0131415 A1 | 6/2005 | Hearn et al. |
| 2005/0205274 A1 | 9/2005 | Bogue |
| 2005/0268750 A1 | 12/2005 | Bruce et al. |
| 2006/0117911 A1 | 6/2006 | Raines, Jr. et al. |
| 2006/0234617 A1 | 10/2006 | Francis et al. |
| 2007/0060933 A1 | 3/2007 | Sankaran et al. |
| 2007/0141110 A1 | 6/2007 | Stone et al. |
| 2007/0179476 A1 | 8/2007 | Shelton et al. |
| 2007/0191915 A1 | 8/2007 | Strother et al. |
| 2008/0004646 A1 | 1/2008 | To et al. |
| 2008/0060487 A1 | 3/2008 | Schell |
| 2008/0133020 A1 | 6/2008 | Blackwell et al. |
| 2008/0153062 A1 | 6/2008 | Beaty et al. |
| 2008/0215060 A1 | 9/2008 | Garcia et al. |
| 2008/0221564 A1 | 9/2008 | Rouiller et al. |
| 2008/0286722 A1 | 11/2008 | Berckmans, III et al. |
| 2009/0014192 A1 | 1/2009 | Ito et al. |
| 2009/0260485 A1 | 10/2009 | Hohmann et al. |
| 2010/0116519 A1 | 5/2010 | Gareis |
| 2010/0204685 A1 | 8/2010 | Ippisch |
| 2010/0222812 A1 | 9/2010 | Stone et al. |
| 2010/0318093 A1 | 12/2010 | Ippisch |
| 2011/0000688 A1 | 1/2011 | Iwata |
| 2011/0190907 A1 | 8/2011 | Porter et al. |
| 2011/0245833 A1 | 10/2011 | Anderson |
| 2011/0288549 A1 | 11/2011 | Steiner et al. |
| 2011/0301611 A1 | 12/2011 | Garcia et al. |
| 2011/0306008 A1 | 12/2011 | Suttin et al. |
| 2011/0306009 A1 | 12/2011 | Suttin et al. |
| 2012/0046665 A1 | 2/2012 | Kim |
| 2012/0067139 A1 | 3/2012 | Pernestal |
| 2012/0116494 A1 | 5/2012 | Leynov et al. |
| 2012/0184958 A1 | 7/2012 | Knuchel et al. |
| 2012/0255756 A1 | 10/2012 | Aoki |
| 2013/0014368 A1 | 1/2013 | Woods et al. |
| 2013/0025892 A1 | 1/2013 | Mashiko et al. |
| 2013/0098646 A1 | 4/2013 | Funabashi et al. |
| 2013/0105189 A1 | 5/2013 | Murthy et al. |
| 2013/0116519 A1 | 5/2013 | Wood |
| 2013/0118323 A1 | 5/2013 | Witte |
| 2013/0165930 A1 | 6/2013 | Lehmann et al. |
| 2013/0193891 A1 | 8/2013 | Wood et al. |
| 2013/0269961 A1 | 10/2013 | Lim et al. |
| 2013/0327552 A1 | 12/2013 | Loveless et al. |
| 2013/0331895 A1 | 12/2013 | Garcia et al. |
| 2013/0331994 A1 | 12/2013 | Ng et al. |
| 2013/0341058 A1 | 12/2013 | Roehm |
| 2014/0048298 A1 | 2/2014 | Fuchs |
| 2015/0182285 A1 | 7/2015 | Yen et al. |
| 2017/0348037 A1 | 12/2017 | Sexson et al. |

FOREIGN PATENT DOCUMENTS

| | | |
|---|---|---|
| JP | H07-124827 A | 5/1995 |
| JP | 2002-283248 | 10/2002 |
| JP | 2005-523174 A | 8/2005 |
| JP | 2012-200807 A | 10/2012 |
| WO | WO 03/090974 A1 | 11/2003 |
| WO | WO 2004/110293 A1 | 12/2004 |
| WO | WO 2008/105057 A1 | 9/2008 |
| WO | WO 2008/128523 A2 | 10/2008 |
| WO | WO 2011/133160 A1 | 10/2011 |
| WO | WO 2015/009850 A1 | 1/2015 |
| WO | WO 2017/214194 A1 | 12/2017 |

OTHER PUBLICATIONS

International Search Report and Written Opinion from corresponding International Application No. PCT/US2014/046884, dated Oct. 22, 2014, 10 pages.

Wadsworth, H., Excerpt from *Handbook of Statistical Methods for Engineers and Scientists*, 2d Ed., 1990.

Brockwell, P., Excerpt from *Introduction to Time Series and Forecasting*, 2d Ed., 2002.

Brown, R.G., Excerpt from *Smoothing, Forecasting and Prediction of Discrete Time Series*, 1963.

Smith, S., Excerpt from "The Scientist and Engineer's Guide to Digital Signal Processing," 2d Ed. 1999.

Sears/Zemansky/Young, Excerpt from "University Physics," 1986.

Gill, P.J., *The Yielding of Fastenings During Tightening*, The Japan Research Institute, vol. 7, No. 12., 1976.

Hsu, et al., *A Modular Mechatronic System for Automatic Bone Drilling*, Biomedical Engineering Applications, Basis, & Communications, vol. 13, No. 4, Aug. 2001.

International Preliminary Report on Patentability from corresponding International Application No. PCT/US2014/046884, dated Jan. 28, 2016, 9 pages.

Extended European Search Report in corresponding European Patent Application No. 14826495.5, dated Jun. 8, 2017, in 5 pages.

Office Action in corresponding Japanese Patent Application No. 2016-527080, dated May 8, 2018, in 7 pages.

(56) References Cited

OTHER PUBLICATIONS

Office Action in corresponding Chinese Patent Application No. 201480040999.0, dated May 31, 2017, in 7 pages.

* cited by examiner

TORQUE-LIMITING SCREWDRIVERS

RELATED APPLICATIONS

This application is a divisional of U.S. patent application Ser. No. 14/332,964, filed Jul. 16, 2014, which claims the benefit of U.S. Patent Application No. 61/856,557, filed Jul. 19, 2013; U.S. Patent Application No. 61/872,427, filed Aug. 30, 2013; U.S. Patent Application No. 61/937,346, filed Feb. 7, 2014; and U.S. Patent Application No. 61/940,197, filed Feb. 14, 2014. The entirety of each of the aforementioned applications is incorporated by reference herein.

BACKGROUND

Field

This disclosure relates to torque-limiting devices, and in particular to embodiments of torque-limiting screwdrivers.

Certain Related Art

Various surgical procedures include inserting one or more screws into a bone to retain a structure, such as a plate, on the bone. During insertion, the screw is threaded into a bone and penetrates into the bone. With continued rotation, the screw seats on the plate, such as by a head of the screw contacting the plate. Still further rotation of the screw secures the screw against the plate and/or further into the bone. However, such further rotation of the screw may cause the screw to strip in the bone, thereby reducing the securement of the screw and the plate.

SUMMARY

It can be beneficial to avoid, or at least inhibit, stripping of the surgical screw in the bone. This can be accomplished with a screwdriver that monitors the torque applied to the screw and stops or reduces the rotation of the screw when certain torque criteria are satisfied. For example, the criteria can include the amount of torque being applied, how the torque is changing over time (e.g., whether the torque is consistently or inconsistently increasing or decreasing), and whether a threshold has been met. The threshold can aid in determining whether the torque being sensed is indicative of the screw being secured against the plate or something else, such as a transitory spike in the torque caused by a localized region of harder bone or otherwise.

Moreover, it can be beneficial to reduce the rotating speed of the screw after certain conditions are satisfied. This can reduce the angular momentum of the screw and/or components of the screwdriver, and thus can reduce the likelihood of unintentional rotation caused by such momentum, even after active driving of the screw has ceased, which can increase the chance of the screw stripping in the bone. Furthermore, reducing the rotational speed of the screw can increase the amount of time available for sensing operations to occur per rotation of the screw. This can facilitate more precise and accurate monitoring of the rotational position of the screw and/or the torque being applied to the screw.

Accordingly, for the reasons indicated above and other reasons, several embodiments of screwdrivers are disclosed. Typically, the screwdriver includes a body and a motor. The motor is operably connected to a drive head at a distal end of the screwdriver such that the motor can turn the drive head. The drive head can receive a bit (e.g., a crosshead bit, flathead bit, star bit (e.g., Torx), socket bit, or otherwise) that can be interfaced with a screw having a head with a corresponding shape. Thus, the screw can be positioned at a desired insertion location on a substrate (e.g., a bone) and the motor can be operated to drive the screw into the substrate. Various embodiments of the screwdriver can limit and/or control torque applied to the screw. Certain embodiments reduce the speed of the screw during the insertion process. Various embodiments provide one or more of the advantages described above, or none of them.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

None of the preceding summary, the following detailed description, and the associated drawings purport to limit or define the scope of protection. The scope of protection is defined by the claims.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments. Various features of the different disclosed embodiments can be combined to form further embodiments, which are part of this disclosure.

DESCRIPTION OF CERTAIN EMBODIMENTS

Figure 1:
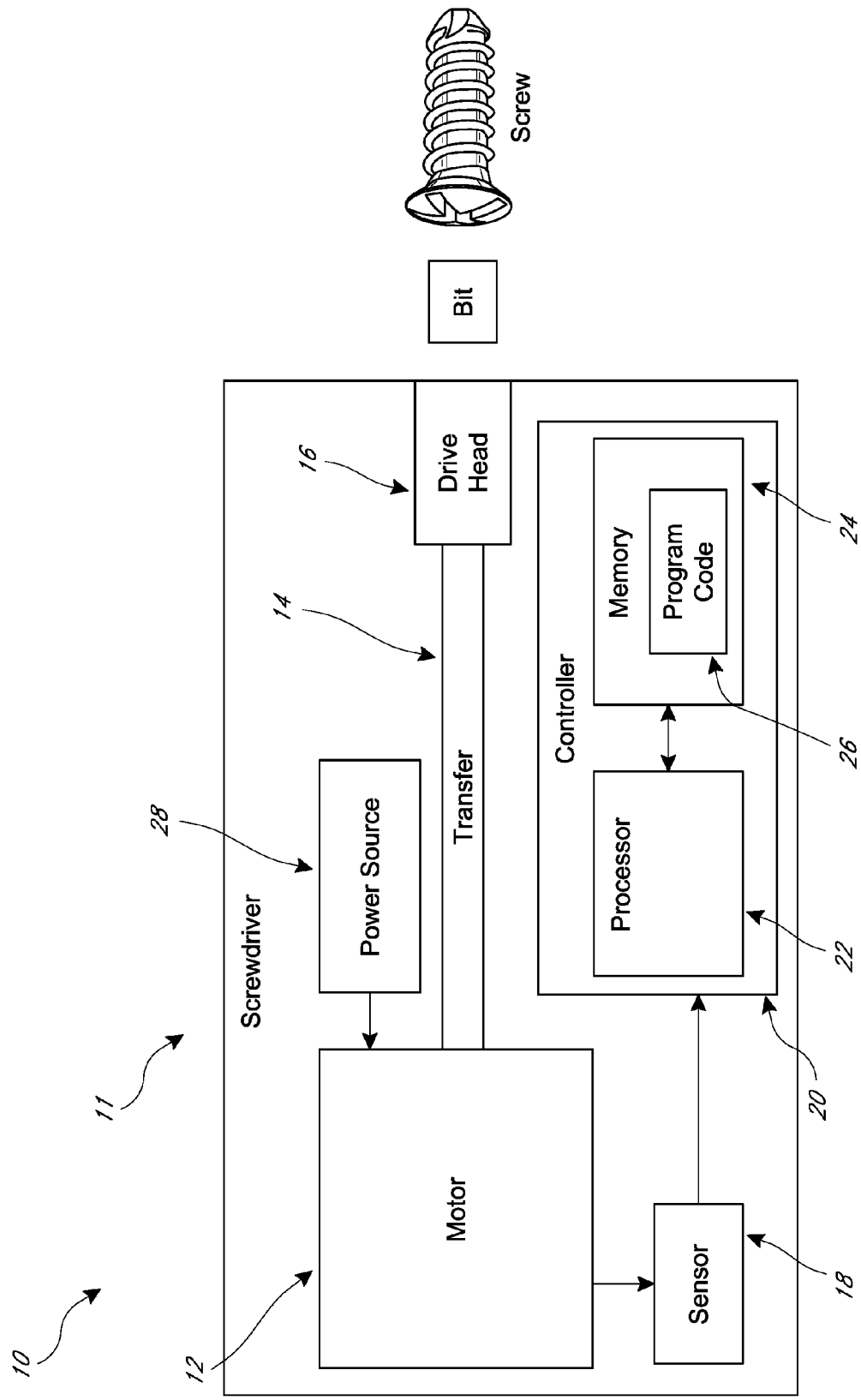
FIG. 1 schematically illustrates an example embodiment of a torque-limiting screwdriver.

Various embodiments of a torque-limiting screwdriver 10 are disclosed. As more fully described below, the screwdriver 10 can determine when to stop a screw being driven into various types of bone so as to avoid stripping the screw in the bone. As shown in FIG. 1, the screwdriver includes a body 11 (also called a housing) that supports a motor 12. A transfer assembly 14 (e.g., one or more shafts, gears, etc.) operably connects the motor 12 to a drive head 16 at a distal end of the screwdriver 10 such that the motor 12 can turn the drive head 16. The drive head 16 can receive a bit, such as a crosshead bit, flathead bit, star bit (e.g., Torx), socket bit (e.g., hex), or otherwise. The bit in turn can be interfaced with a screw having a head with a corresponding shape. Thus, the screw can be positioned at a desired insertion location on a substrate (e.g., a bone) and the motor 12 can be operated to drive the screw into the substrate.

The screwdriver 10 can monitor and/or limit the torque that the screwdriver 10 is applying to the screw during the insertion process. For example, as described in more detail below, the screwdriver 10 can include a sensor 18 that senses the current supplied to the motor 12. The sensor 18 can send such data to a controller 20, which can include a processor 22 coupled with a memory 24. Because the current supplied to the motor 12 can be proportional to the torque applied to the screw, the controller 20 can dynamically determine the amount of torque being applied to the screw. In certain variants, the controller 20 is configured to determine or receive signals indicative of one or more of the following data features: current supplied to the motor 12, number of revolutions of the screw and/or motor, distance traveled by the screw (e.g., into the bone), speed of the motor 12, or otherwise.

As described in more detail below, various embodiments of the screwdriver 10 include an algorithm adapted to limit and/or control the torque applied to the screw. This can enable the screwdriver 10 to be used with different screw sizes and different bone densities. The algorithm can be included in the memory 24 as program code 26 that be implemented on a computer-readable non-transitory medium. The processor 22 can execute the program code 26 to perform various operations, such as determining a torque limit, instructing the motor to cease operation, instructing a power source 28 to reduce and/or stop providing power to the motor 12, or other operations.

Figure 2:
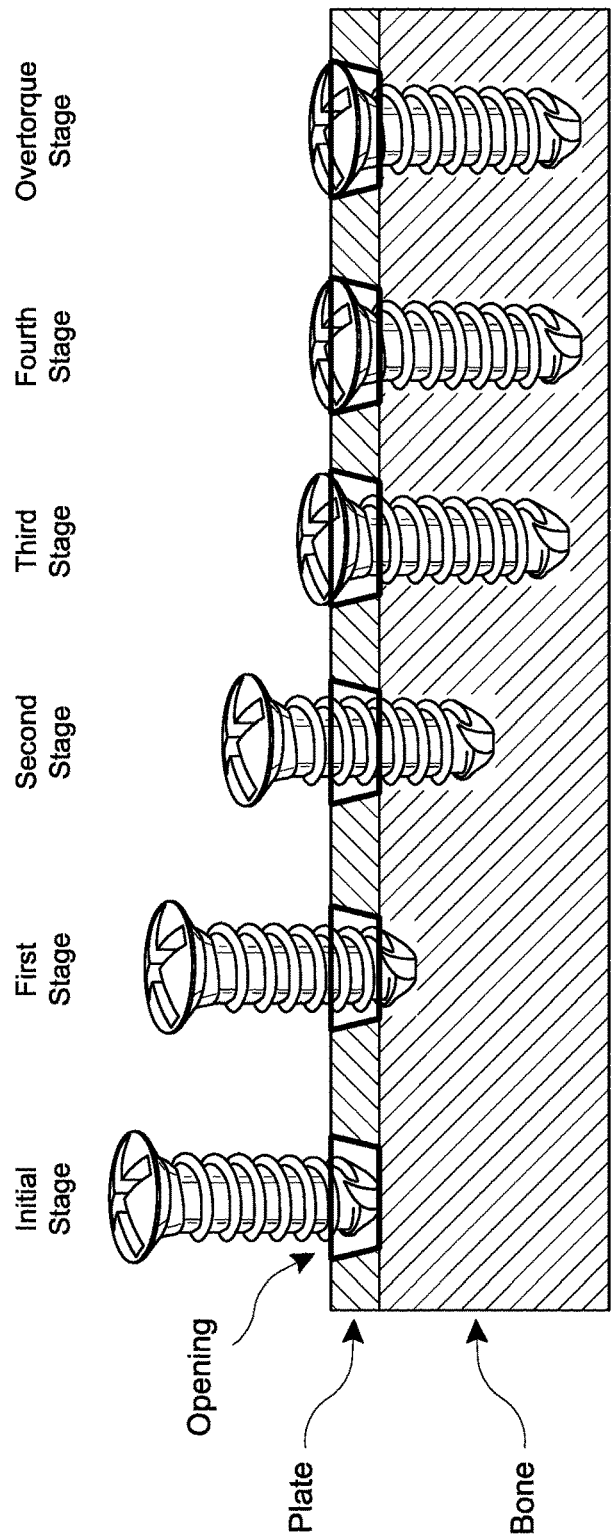
FIG. 2 schematically illustrates various stages in the process of inserting a screw into a bone.
Figure 2A:
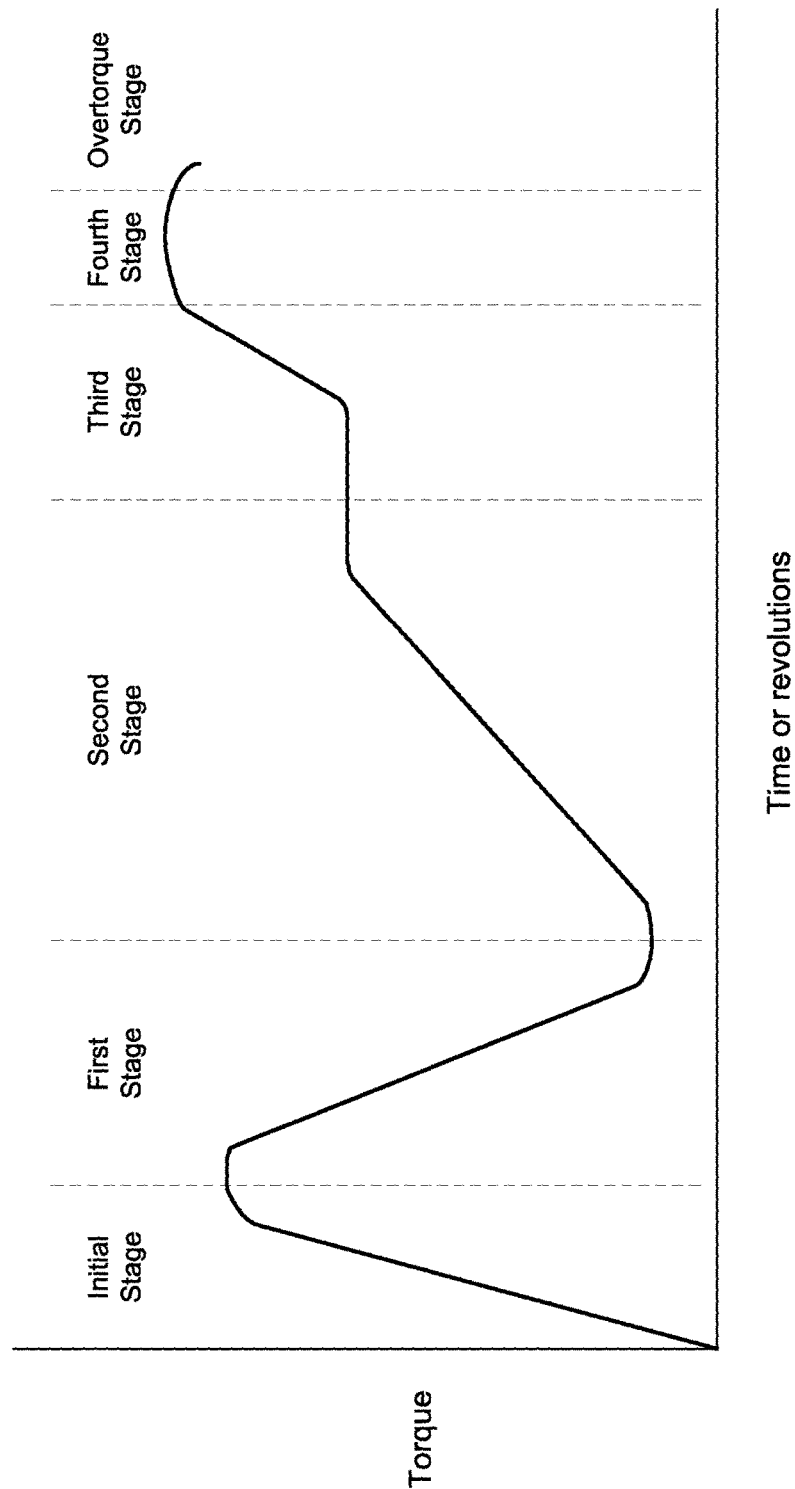
FIG. 2A illustrates an example plot of torque as a function of time or revolutions during insertion of a screw into a bone.
Figure 2B:
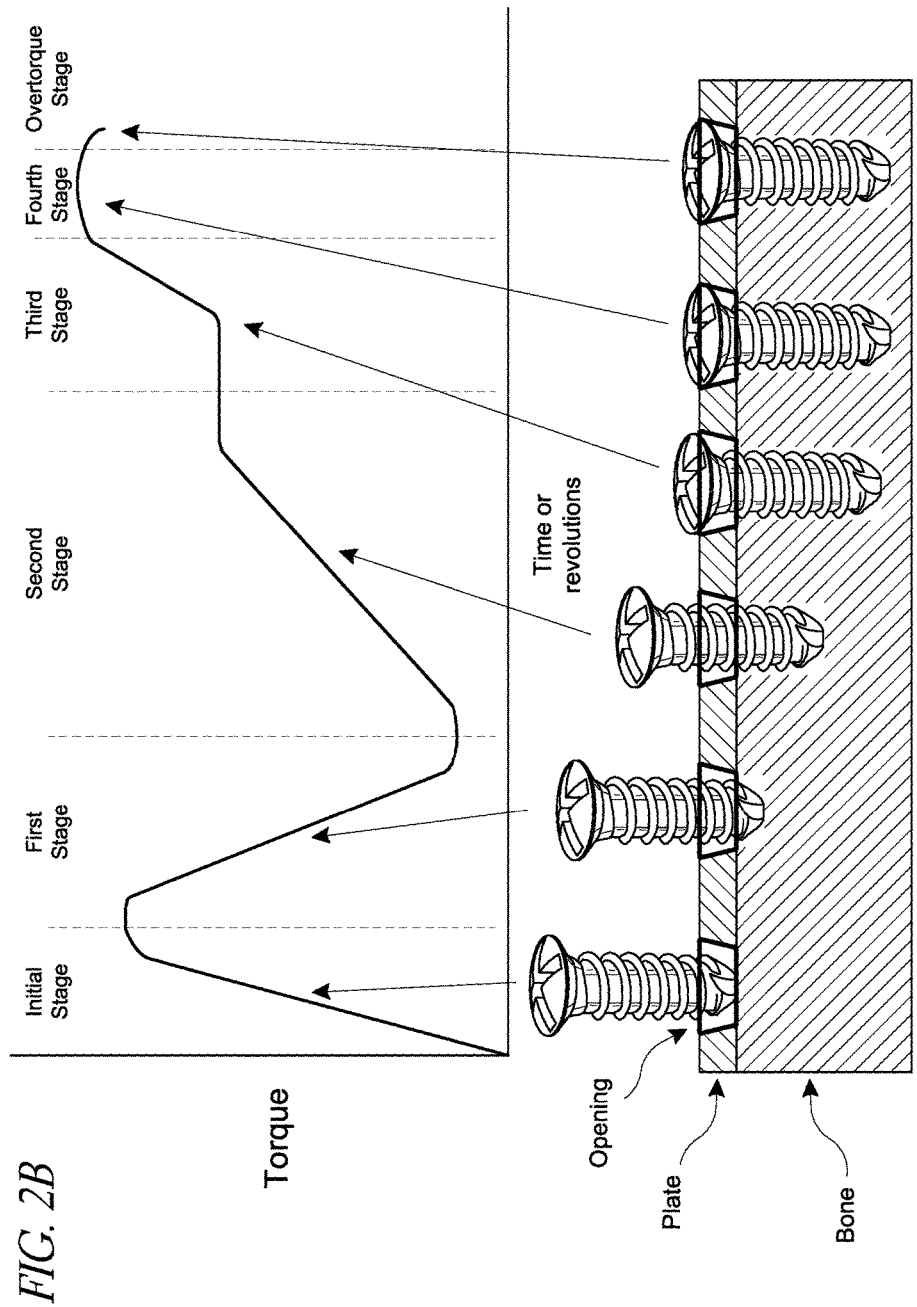
FIG. 2B illustrates the relationship of the stages of FIG. 2 to the plot of FIG. 2A.

Overview of the Screw Insertion Process (FIGS. 2, 2A, and 2B)

The process of inserting a screw into a bone to secure a plate against the bone includes several steps. As shown in FIG. 2, in an initial stage, the screw is positioned through an opening in the plate and adjacent to the bone at the desired insertion location. Also, the screw can be coupled with the screwdriver 10 discussed above, which can begin rotating the screw relative to the bone. As the screw rotates, it begins to cut into the bone, which provides space for the screw's body to be inserted. For screws that are self-tapping, the screw can begin to push material outwardly, thereby creating a path into the bone. To facilitate this process, the user can apply some axial force to the screw, such as via the screwdriver 10. As illustrated, during the initial stage, the torque gradient can exhibit a steep upward (e.g., positive) slope and the rotational speed of the screw is reduced (e.g., compared to the speed at no load).

After the initial stage concludes, a first insertion stage begins. In the first stage, the screw body moves axially into the bone via the path created in the initial stage. As shown in FIG. 2A, during the first stage, the torque gradient can have a downward (e.g., negative) slope and the rotational speed of the screw can increase compared to the later part of the initial stage.

In the second stage, the screw continues advancing into the bone following the path created by the entry threads. Typically, the screw advances substantially the entire or the entire thread length of the body of the screw (less the axial thickness of the plate) into the bone. In some implementations, the torque vs. time (or torque vs. revolutions of the screw) curve will have a positive torque gradient as the screw advances the length of the thread.

The third stage begins when the screw head initially seats against the plate. As illustrated, the screw typically has a head that is larger in diameter than at least a portion of the opening in the plate. Thus, during the third stage, the head can contact the plate and inhibit or prevent the screw from passing further through the plate. This can result in an initial sharp increase of the torque curve. As shown in FIG. 2A, during the third stage, the torque gradient can be upward (e.g., positive). For example, the slope can be less than the slope of the initial stage but greater than the slope of the second stage. In certain implementations, the later part of the third stage, the torque gradient exhibits a flattening (e.g., reaches a plateau) and/or includes a crest, such as a localized maximum torque that is less than the torque at an inflection point during a fourth stage, which is discussed below. In certain variants, the rotational speed of the screw during the third stage is less than the speed during the second stage.

In the fourth stage, the screw is fully seated on the plate, thereby fixedly securing the screw, bone, and plate. This can include the head of the screw being partly or completely received into the opening of the plate and inhibited or prevented from further axial movement into the bone by the plate. As illustrated in FIG. 2A, during the fourth stage, the torque can continue increasing, though at a rate that is less than the rate of the third stage. For example, the slope of the curve in the fourth stage can be less than the slope in the third stage (e.g., at the end of the third stage). The torque can reach a peak during the fourth stage, after which the torque begins decreasing. In some implementations, the rotational speed of the screw in the fourth stage is less than the rotational speed of the screw in the initial, first, second, and third stages.

In an overtorque stage, which can occur after the fourth stage, an additional amount of torque can be applied to the screw to further tighten the screw in the bone. This can slightly overtorque the screw in the bone (e.g., violate a yield strength of the screw and/or the bone). Too much overtorque is undesirable as it can cause the screw to strip. But a relatively small amount can be beneficial, because it can result in slight deformation of the screw and/or the bone, which can aid in maintaining the screw in its position, and thus inhibit or prevent the plate from moving relative to the bone. In various implementations, the overtorqueing is accomplished by rotating the screw a final amount. For example, the screw can be rotated about one rotation, about ½ of a rotation, about ¼ of a rotation, about ⅛ of a rotation, values in between, or otherwise. In some embodiments, the amount that the screw is overtorqued is at least 1 Newton centimeter (N-cm) and/or less than or equal to about 5 N-cm.

Certain aspects of the stages of the insertion process are summarized below in Table A:

TABLE A

| Stage | Torque | Torque Gradient | Speed | Observations |
|---|---|---|---|---|
| Initial Stage: Screw driving initiation and bone engagement | Initially no load and no torque | Steeply positive | High | Increasing values. Large noise to signal ratio |
| First Stage: Screw advancement starts | Initially high | Negative | High | Decrease or leveling off values |

TABLE A-continued

| Stage | Torque | Torque Gradient | Speed | Observations |
| --- | --- | --- | --- | --- |
| Second Stage: Screw inside bone and continue advancing | Initially low | Positive | Reducing | Smooth continuous increasing values |
| Third Stage: Screw seated on plate | Middle | Flat to positive | Mid | Small plateau or distinct increase of values |
| Fourth Stage: Screw compressing plate against bone | High | Level and/or negative | Low | Cresting, plateau of values |
| Overtorque Stage: Screw seated on plate and additional torque applied | High to Middle | Negative | Low | Decreasing values |

Typically, to remove the screw from the bone, and to free the plate, the screwdriver 10 can be interfaced with the head of the screw and the rotation of the screw reversed. Because the screw is not cutting into the bone and is not being tightened against the bone or plate, the torque on the screw during a removal operation is normally less than during the insertion process described above.

Figure 3:
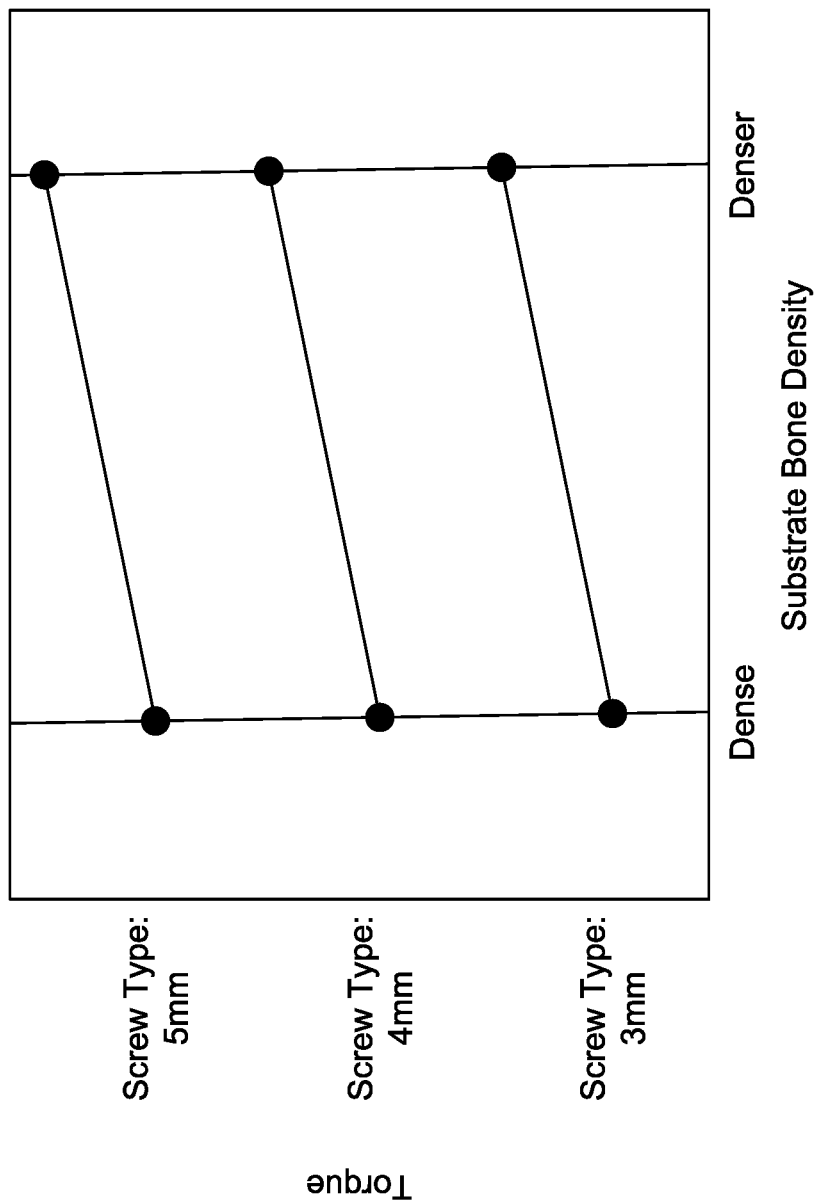
FIG. 3 illustrates a plot of example torques on 3 mm, 4 mm, and 5 mm screw types as a function of bone density.

Certain Variables That Affect Torque (FIG. 3)

The torque needed to insert the screw in a given bone can vary significantly. One factor that affects the amount of torque required to insert the screw into a bone is the density of the bone, which can change based on age, gender, disease, and other factors. Typically, the denser the bone, the greater the force required to insert the screw. Another factor that affects the amount of torque required to insert the screw into a bone is the specifics of the screw, such as the diameter, length, thread type (e.g., shape and/or number of threads per inch), material, coefficient of friction with the bone, and other features. Generally, the longer the screw (e.g., an axial length of at least about: 3 mm, 4 mm, 5 mm, or otherwise), the more torque required to insert the screw to a fully installed position.

FIG. 3 shows illustrative example torques on 3 mm, 4 mm, and 5 mm screw types as a function of bone density. As shown, there can be different torque requirements based on the size and type of the screw and the bone density substrate against which the screw is inserted. This can cause issues in using a fixed torque limit. For example, if the torque limit is fixed based on a dense bone substrate and the smaller (e.g., 3 mm) screw, then a larger (e.g., 5 mm) screw inserted on a denser bone substrate may not seat completely. On the other hand, if the torque limit is fixed based on a larger (e.g., 5 mm) screw and denser substrate, the smaller (e.g., 3 mm) screw on a less dense substrate may strip during insertion.

Fixed Torque-Limiting Embodiments

Certain screwdrivers include a fixed torque value for a specific screw type. For example, for a 3 mm screw, the screwdriver 10 can include a torque limit set at a value that is specific to that type of screw and to the particular type of bone the screw is to be inserted into. For a screwdriver 10 configured to receive and drive three types of screws (e.g., 3 mm, 4 mm, and 5 mm), the screwdriver 10 would include three torque limit values. The values can be determined by experimentation for each screw type with each substrate.

Variable Torque-Limiting Embodiments (FIGS. 4-8)

Various embodiments of the screwdriver 10 use an algorithm to dynamically determine the torque limit and/or when to stop rotation of the screw. This can allow the screwdriver to account for insertion variables (e.g., the density of the bone and the screw specifics) so as to correctly seat the screw, while also inhibiting or preventing the screw from stripping. In several embodiments, the insertion variables do not need to be input into the screwdriver. Rather, certain embodiments of the screwdriver 10 can determine when the screw is properly installed and/or can avoid stripping of the screw based on the torque required to turn the screw in relation to other parameters, such as the time that the screwdriver 10 has been rotating the screw and the amount of torque that has already been applied to the screw.

Several torque-limiting methods, algorithms, and components are described below. Any method, algorithm, or component disclosed anywhere in this specification can be used in conjunction with any other method, algorithm, or component disclosed anywhere in this specification, or can be used separately.

Differential Torque Comparisons

Figure 4:
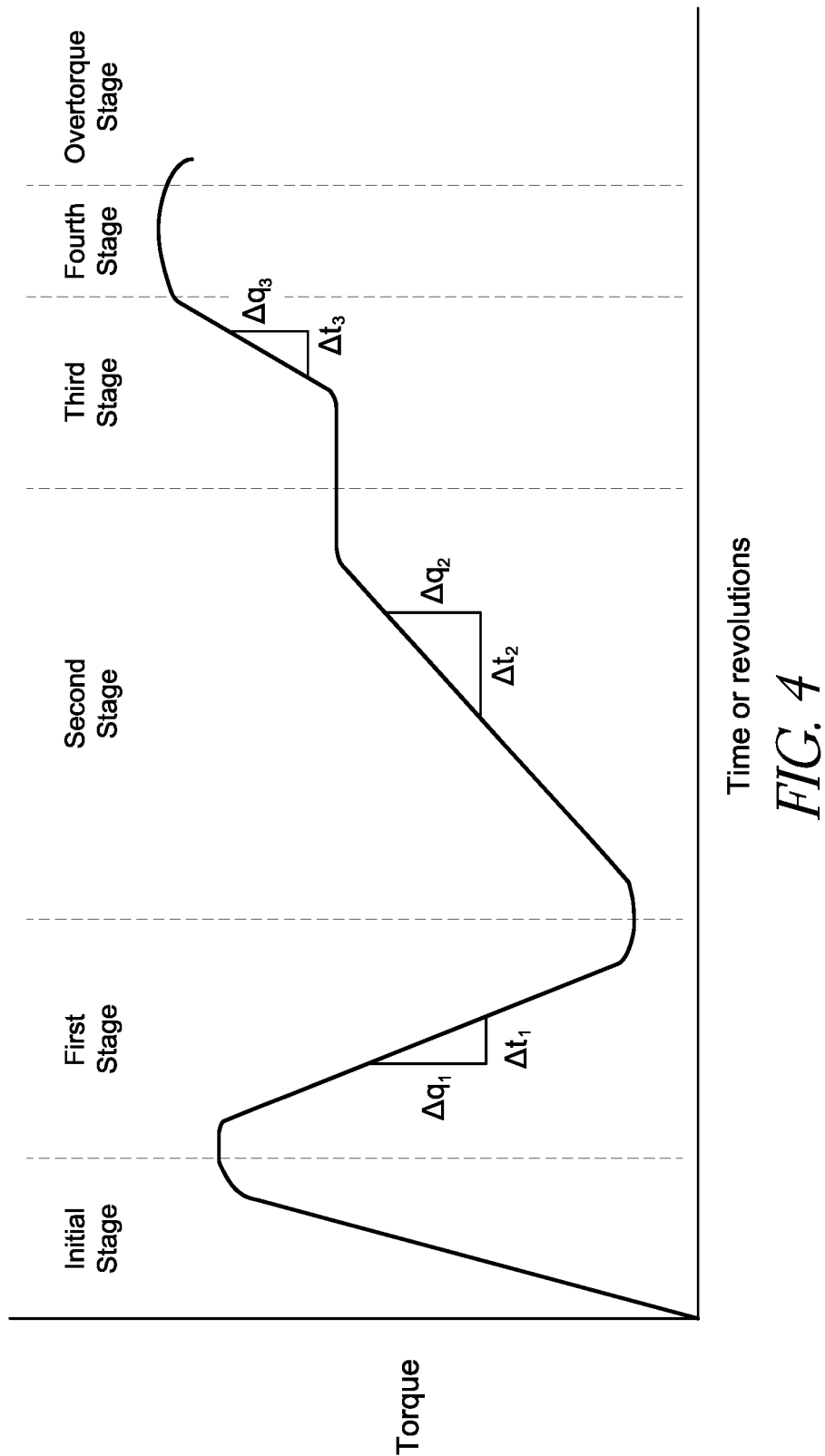
FIG. 4 illustrates a torque plot with comparative torque regions.

In some embodiments, the algorithm compares how the torque has changed during certain portions of the insertion operation. To facilitate this comparison, the controller 20 can calculate discreet changes in the torque during the course of insertion of the screw (e.g., torque as a function of time). For example, as shown in FIG. 4, the controller 20 can determine $\Delta q$ values and $\Delta t$ values throughout some or all of the insertion of the screw, where $\Delta q$ is the change in torque and $\Delta t$ is the change in time, depth, or revolution of the screw. Certain embodiments use a relationship of the $\Delta q$ values and $\Delta t$ values during the insertion stages of the screw. For example, some implementations engage a torque-limiting feature (e.g., stop the motor) when the following comparison is met:

$$\frac{\Delta q3}{\Delta t3} > \frac{\Delta q2}{\Delta t2} > \frac{\Delta q1}{\Delta t1}$$

Such an algorithm can enable the screwdriver 10 to limit the torque while also accounting for certain aspects of the insertion process. For example, this algorithm can include and/or consider that the torque starts at low level and a high level of speed. Certain embodiments of the algorithm include and/or consider that, when the screw is being threaded into bone, the torque may increase and the reduction in speed may decrease. Some variants of the algorithm include and/or consider that, when the screw seats on the plate, the torque may increase and the speed may decrease. Various embodiments of the algorithm are configured to inhibit or avoid the failure mode of stripping of the screw.

In certain embodiments, a measured amount of torque (or current drawn by the motor) is sampled, such as about every 10 milliseconds (ms), 20 ms, or other time values. The torque and time data can be stored in the memory. This can facilitate monitoring the change in the torque relative to time (e.g., a first derivative of the torque). As noted above, the torque can be directly proportional to the motor power required to insert the screw. In several embodiments, the torque at a given time is determined by the controller 20, which receives a signal from the sensor 18 indicative of the current drawn by the motor 12.

Consecutive Torque Values, Thresholds, and Slowdowns

In some embodiments, the methods and algorithms activate (e.g., engage) torque-limiting functionality when a number of values meet a condition. For example, as discussed in more detail below, the screwdriver 10 can monitor the torque for a number (e.g., three) of consecutive decrementing values and can reduce and/or stop rotation of the screw (e.g., by reducing or stopping power to the motor 12) in response to such a condition being met.

Figure 5:
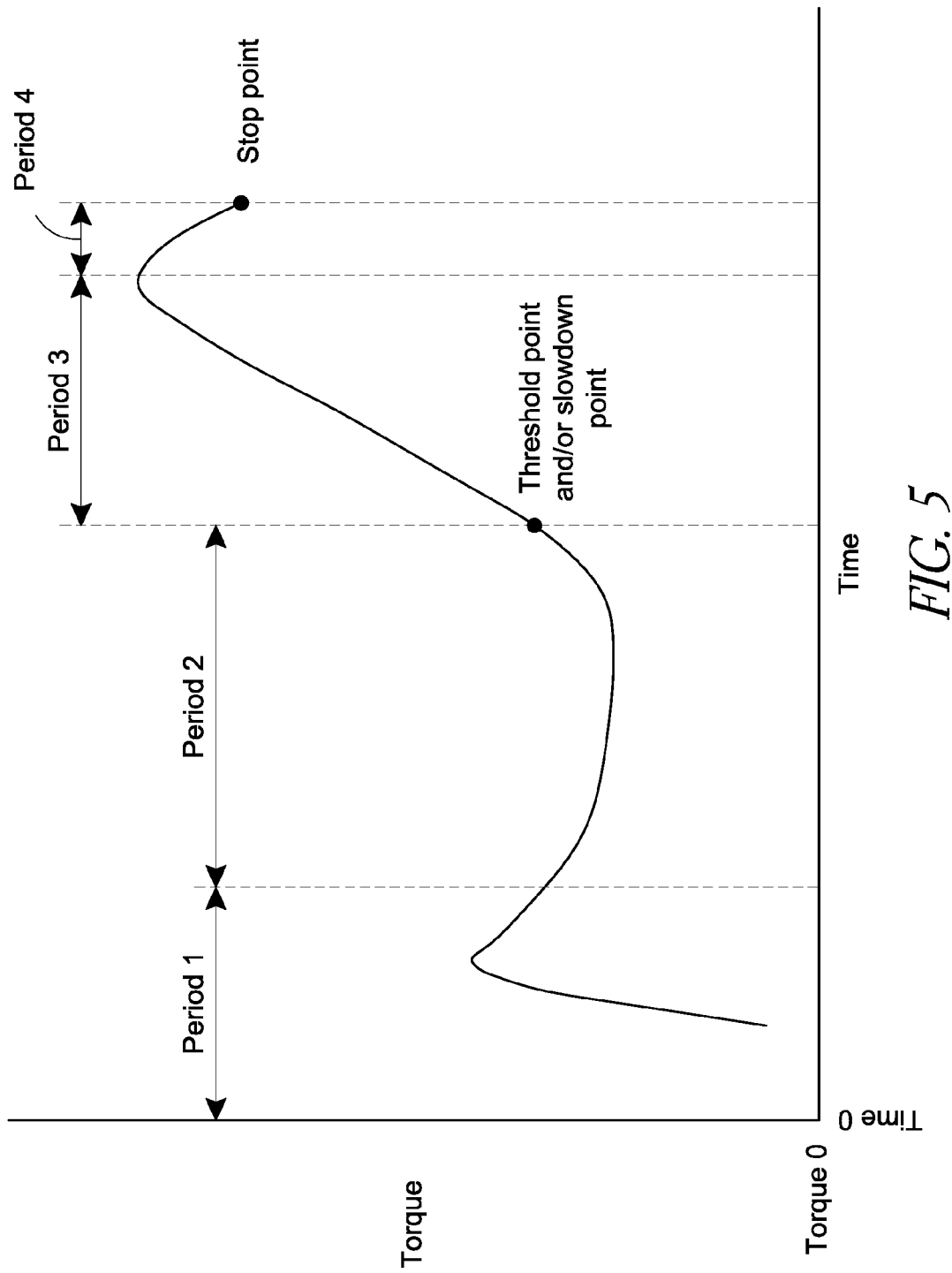
FIG. 5 illustrates a torque plot with threshold and slow-down points.

FIG. 5 shows an illustrative torque versus time curve. As shown, the torque curve can be divided into several periods, such as Period 1, Period 2, Period 3 and Period 4. In some embodiments, Period 1 (e.g., the initial stage as discussed above) includes the initial engagement and entry of the screw into a substrate, such as a bone. During this period, the amount of torque can increase rapidly. Period 1 may also include an increased level of noise and/or unpredictable or unreliable torque data. As such, in some embodiments, the torque data measured during Period 1 is not used to control operation of the driver. Rather, the torque data during Period 1 is ignored or recorded only. Period 1 is thus referred to as a "deadband." In some embodiments, the deadband extends for at least about 50 ms and/or less than or equal to about 200 ms after Time 0 (e.g. the beginning of the screw insertion process at which the screw begins penetrating into the bone). In certain embodiments, the deadband has a duration of less than or equal to about 100 ms.

Period 2 occurs at the conclusion of Period 1. During Period 2 (e.g., the second stage as discussed above), the screw is in the process of threading into the substrate and may experience less torque than the initial torque experienced during Period 1. In some variants, the torque data of Period 2 is not used for torque-limiting purposes but is recorded or logged.

In Period 3 (e.g., similar to the third stage and about the first half of the fourth stage discussed above), the torque on the screw can increase. This is because, for example, the screw engages a plate, and begins tightening the plate against the bone. In some embodiments, a threshold point (e.g., threshold condition) is reached during insertion of the screw, such as at or near the beginning of Period 3. In some embodiments, the screwdriver 10 renders torque-limiting functionality activatable in response to reaching the threshold point. For example, if a torque-limiting condition is experienced prior to reaching the threshold point, the torque-limiting functionality is not activated. In comparison, after the threshold point has been reached, if a torque-limiting condition occurs, then the torque-limiting functionality can be activated. This can avoid erroneous and/or transitory torque values activating the torque-limiting functionality, which could result in premature stopping of the screwdriver 10 and/or incomplete insertion of the screw. In certain implementations, the threshold point can act as a gate, whereby the torque-limiting functionality can be engaged only at or after the torque applied to the screw reaching the threshold point.

In some embodiments, the threshold point is a function of torque and/or current. For example, threshold point can be a torque value of at least about: 5 N-cm, 7 N-cm, 10 N-cm, 12 N-cm, 15 N-cm, 17 N-cm, 20 N-cm, 25 N-cm, values between the aforementioned values, or other values. In certain variants, the threshold point occurs at a torque of greater than or equal to about 5 N-cm and/or less than or equal to about 15 N-cm. In some embodiments, in response to the torque applied to the screw meeting, or exceeding, the torque value of the threshold point, then the torque-limiting functionality is able to be engaged. As noted above, the torque can be determined from the current drawn by the motor 12. In some embodiments, the threshold point is met or exceeded when the electrical current drawn by the motor 12 is at least about: 0.25 A, 0.50 A, 0.75 A, 1 A, 1.25 A, 1.5 A, 1.75 A, 2 A, 2.5 A, 3 A, values between the aforementioned values, or other values. In certain implementations that include a polyphase motor (e.g., a 3-phase motor), the average total forward current of the phases is used in determining the current. Some implementations use a direct-quadrature-zero transformation or Park's Transformation in determining the current.

In some embodiments, the threshold point is a function of time. For example, in certain variants, the threshold point occurs a certain amount of time from Time 0. In some embodiments, the threshold point occurs at least about 300 ms and/or less than or equal to about 500 ms from Time 0. In certain variants, the threshold point occurs at greater than or equal to about 200 ms after Time 0.

With continued reference to FIG. 5, the screwdriver 10 can include a slowdown point (e.g., a slowdown condition). In some embodiments, the screwdriver 10 changes the speed at which it rotates the screw in response to the slowdown point being, or having been, reached. For example, prior to reaching the slowdown point, the screwdriver 10 may operate at first speed (e.g., greater than or equal to about 3600 rpm) and after reaching the slowdown point, the screwdriver 10 can operate at a second rotational speed (e.g., less than or equal to about 900 rpm). In some embodiments, the slowdown results in a delay of the full insertion of the screw of at least about: 0.10 second, 0.25 second, 0.50 second, 0.75 second, 1 second, 1.5 seconds, values between the aforementioned values, or other values. Certain implementations of the screwdriver 10 can increase the total time it takes to insert the screw, such as by at least the aforementioned time values. Other implementations of the screwdriver 10 do not increase the total insertion time. For example, some variants increase the insertion speed (and reduce the insertion time) before the slowdown point a sufficient amount to counteract the reduction in speed (and increase in insertion time) after the slowdown point.

Reducing the insertion speed (e.g., rotational speed) of the screw can be beneficial. For example, this can reduce the rate at which the torque increases during insertion of the screw. In some embodiments, reducing the insertion speed improves monitoring and/or resolution of the torque applied to the screw by the screwdriver 10 during the screw insertion process (e.g., during Period 3 and/or Period 4), such as by providing additional time for the processor 22 and/or sensor 18 (e.g., current sensor) to monitor the amount of torque on the screw and/or to determine whether the torque-limiting functionality should be activated. For example, a reduction in the speed from about 3600 rpm to about 900 rpm can increase the duration of Period 3 and/or Period 4 by a factor of about 4. In some embodiments, the slowdown results in an increase in resolution of the monitored torque (e.g., of the motor's current draw detected by the sensor 18) of at least about: 2, 3, 4, 5, 6, values between the aforementioned values, or other values.

In some implementations, the reduction in rotational speed can provide a more accurate and/or precise rotation of the screw relative to the substrate. For example, a reduction in the rotational speed of the motor, drive train and/or screw can reduce the momentum of those components. In some embodiments, this can reduce the likelihood of error, such as error caused by unintended rotation from that momentum. In some embodiments, the slowdown results in the rotational momentum of the screw being reduced at least about: 50%, 100%, 200%, 300%, 400%, 500%, values between the aforementioned values, or other values.

In certain variants, the reduction in speed of the screw can provide an indication to a user, such as a surgeon. For example, the reduction can provide a signal that a certain amount of torque has been reached, that the threshold point has been or is about to be reached (e.g., within less than or equal to about 0.75 second), that the torque-limiting point is about to be reached (e.g., within less than or equal to about 1 second), and/or that the screwdriver 10 is about to stop driving the screw. In some embodiments, the slowdown is accompanied by an indicator, such as the activation of a light (e.g., an LED), an audible sound, or other sensory indicator.

In some embodiments, the slowdown point is a function of torque and/or current. For example, slowdown point can be a torque value of at least about: 5 N-cm, 7 N-cm, 10 N-cm, 12 N-cm, 15 N-cm, 17 N-cm, 20 N-cm, 25 N-cm, values between the aforementioned values, or other values. In certain implementations, the slowdown point occurs at a torque of greater than or equal to about 5 N-cm and/or less than or equal to about 15 N-cm. In some embodiments, the screwdriver 10 engages the speed-reduction functionality in response to the torque on the screw meeting, or exceeding, the torque value of the slowdown point. As previously discussed, the torque can be determined from the current drawn by the motor 12. In some embodiments, the slowdown point is reached when the electrical current drawn by the motor 12 is at least about: 0.25 A, 0.50 A, 0.75 A, 1 A, 1.25 A, 1.5 A, 1.75 A, 2 A, 2.5 A, 3 A, values between the aforementioned values, or other values. Some implementations that include a polyphase motor (e.g., a 3-phase motor) use the average total forward current of the phases in determining the current. Certain variants use a direct-quadrature-zero transformation or Park's Transformation in determining the current.

In some embodiments, the slowdown point is a function of time. For example, in certain variants, the slowdown point occurs a certain amount of time from Time 0. In some embodiments, the slowdown point occurs at least about 300 ms and/or less than or equal to about 500 ms from Time 0. In certain variants, the slowdown point occurs at greater than or equal to about 200 ms after Time 0.

In some embodiments, the threshold point and the slowdown point are the same point. For example, as shown, both the threshold point and the slowdown point can occur at the beginning of Period 3. In some implementations, this is determined by an amount of time from Time 0, such as at least about: 150 ms, 200 ms, 250 ms, 300 ms, 350 ms, 400 ms, 500 ms, values between the aforementioned values, or other values. In other embodiments, the threshold point and the slowdown point are different points. For example, in some embodiments the slowdown point occurs before the threshold point; in other embodiments the slowdown point occurs after the threshold point. In some implementations, the threshold point and the slowdown point are separated by an amount of time (e.g., less than or equal to about 100 ms).

In some embodiments, the threshold point and the slowdown point are separated by an amount of torque (e.g., less than or equal to about 3 N-cm).

As illustrated, Period 4 (e.g., similar to about the second half of the fourth stage and the overtorque stage discussed above) begins after Period 3 ends, such as at about the apex of the torque curve. Period 4 can include a decrease in the torque (e.g., a negative torque gradient). This can suggest that yielding and/or stripping of the screw and/or the substrate is imminent or has begun. In some embodiments, the screwdriver 10 monitors the torque data for N consecutive decreasing torque values. For example, in some implementations, N equals 2, 3, 4, 5, 6, 7, or otherwise. In an embodiment in which N is 4, the torque-limiting condition would be satisfied when 4 consecutive decreasing torque values are observed. In various embodiments, after the torque-limiting condition has been satisfied and the threshold point has been passed, the torque-limiting algorithm can instruct that the screwdriver 10 cease turning the screw. For example, power to the motor 12 can be reduced or eliminated.

Figure 6:
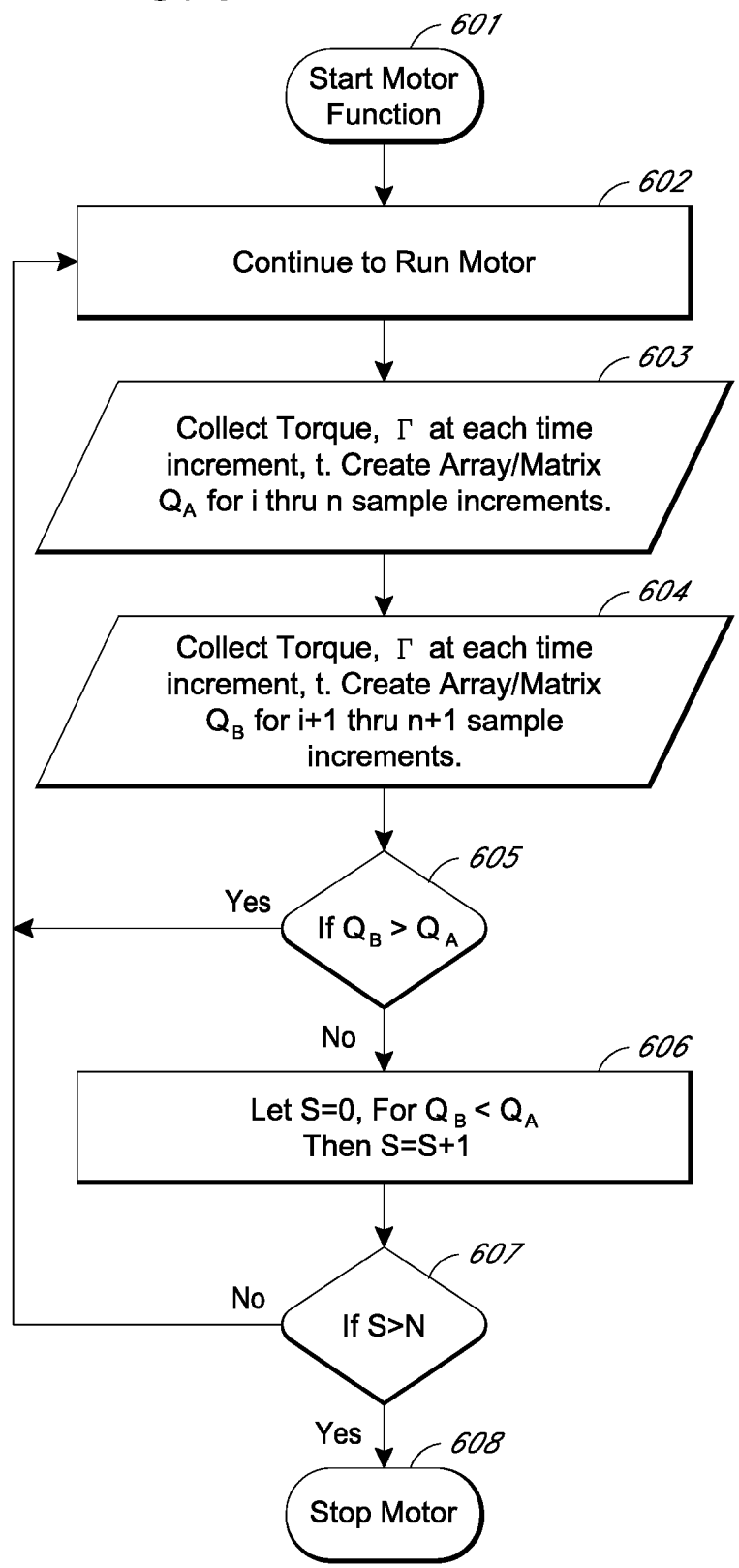
FIG. 6 illustrates a process of monitoring and controlling torque during a screw driving operation.

FIG. 6 illustrates another embodiment of a torque-limiting method and algorithm. In this algorithm:
t is the time increment in microseconds;
I is the current sampling;
$\Gamma$ is the torque, which is proportional to the current sample;
i is the time increment of the system sample;
n is the array length;
Q is $d\Gamma/dt$; and
S is a count variable.
The algorithm can include arrays, such as:

$$\overline{Q}_A = \begin{vmatrix} \Gamma_i & \ldots & \Gamma_n \\ t_i & \ldots & t_n \end{vmatrix}$$

$$\overline{Q}_B = \begin{vmatrix} \Gamma_{i+1} & \ldots & \Gamma_{n+1} \\ t_{i+1} & \ldots & t_{n+1} \end{vmatrix}$$

As illustrated, in a first block 601, the motor 12 can be started. For example, in response to a user activating an input (e.g., a button or switch), the controller 20 on the screwdriver 10 can instruct that power be supplied to the motor 12 to begin turning the screw. In some embodiments, the motor 12 continues to run in at least a second block 602.

In various embodiments, torque values are collected (e.g., observed and recorded). In this regard, various embodiments detect (e.g., with a sensor 18) the amount of current being drawn by the motor 12. This current draw data can be used to determine the amount of torque because the current drawn by the motor 12 is generally proportional to the amount of torque that the motor is applying to a screw being driven by the screwdriver 10. As shown, in block 603, a torque amount at each time increment can be collected and stored in the memory 24. This torque and time data can be used to create an array or matrix $Q_A$ for i through n sample increments. In a subsequent block 604, further torque values can be collected for additional time increments, and that further time and torque data can be used to create another array or matrix $Q_B$.

Some embodiments include a comparison block 605, in which $Q_A$ and $Q_B$ are compared. In certain implementations, if $Q_B$ is greater than $Q_A$, then the algorithm returns to an earlier block, such as block 602. This can allow additional arrays $Q_A$ and $Q_B$ to be created and compared. Accordingly, in some embodiments, the comparison of arrays $Q_A$ and $Q_B$ is substantially constantly occurring in a loop during implementation of the algorithm.

As illustrated, if $Q_B$ is not greater than $Q_A$, then an iterative portion of the algorithm can be performed. In some embodiments, this includes initializing and/or incrementing a count variable S. For example, for each time the algorithm determines that $Q_B$ is not greater than $Q_A$, then the algorithm can proceed to block 606, in which the count variable S is increased by 1.

As shown, in block 607, the count variable S is compared to a preset number N of allowable consecutive decreasing torque values (e.g., 2, 3, 4, 5, 6, or otherwise). For example, if the count variable S is not greater than the number N, then the algorithm can return back to an earlier block (e.g., block 602). Additional $Q_A$ and $Q_B$ arrays can be created and compared in blocks 603-605. On returning to block 605, if $Q_B$ is still not greater than $Q_A$, then the algorithm can proceed to block 606 and the count variable S is increased by 1 again. In various embodiments, if $Q_B$ is greater than $Q_A$, then the count variable S is initialized (e.g., S=0).

In certain embodiments, if the count variable S is greater (or greater than or equal to in some variants) than N consecutive decreasing torque values, then the algorithm proceeds to block 608, in which a torque-limiting function can be activated. For example, the controller 20 can issue an instruction that the motor 12 should be stopped (e.g., by eliminating or reducing the power supplied to the motor). Thus, the torque being applied to the screw can be controlled and/or limited.

According to various embodiments, if fewer than N consecutive decreasing torque values are observed, the motor 12 continues to operate. This can reduce the likelihood that the torque-limiting algorithm will prematurely stop the driving of the screw. For example, by not stopping the motor 12 unless at least N consecutive decreasing torque values are observed, premature stoppage of the motor due to noise in the current signal or transitory torque reductions can be avoided.

In some embodiments, if the count variable S is greater than or equal to a preset number N of consecutive decreasing torque values, then the motor is stopped. For example, if N equals 4, then the motor is stopped when the count variable S is greater than or equal to 4 (e.g., four consecutive iterations through blocks 602-606 in which the torque values decrease each time). Otherwise, in some embodiments, the motor continues running and driving the screw.

Zone of Tolerance and Peak Determination

Figure 7:
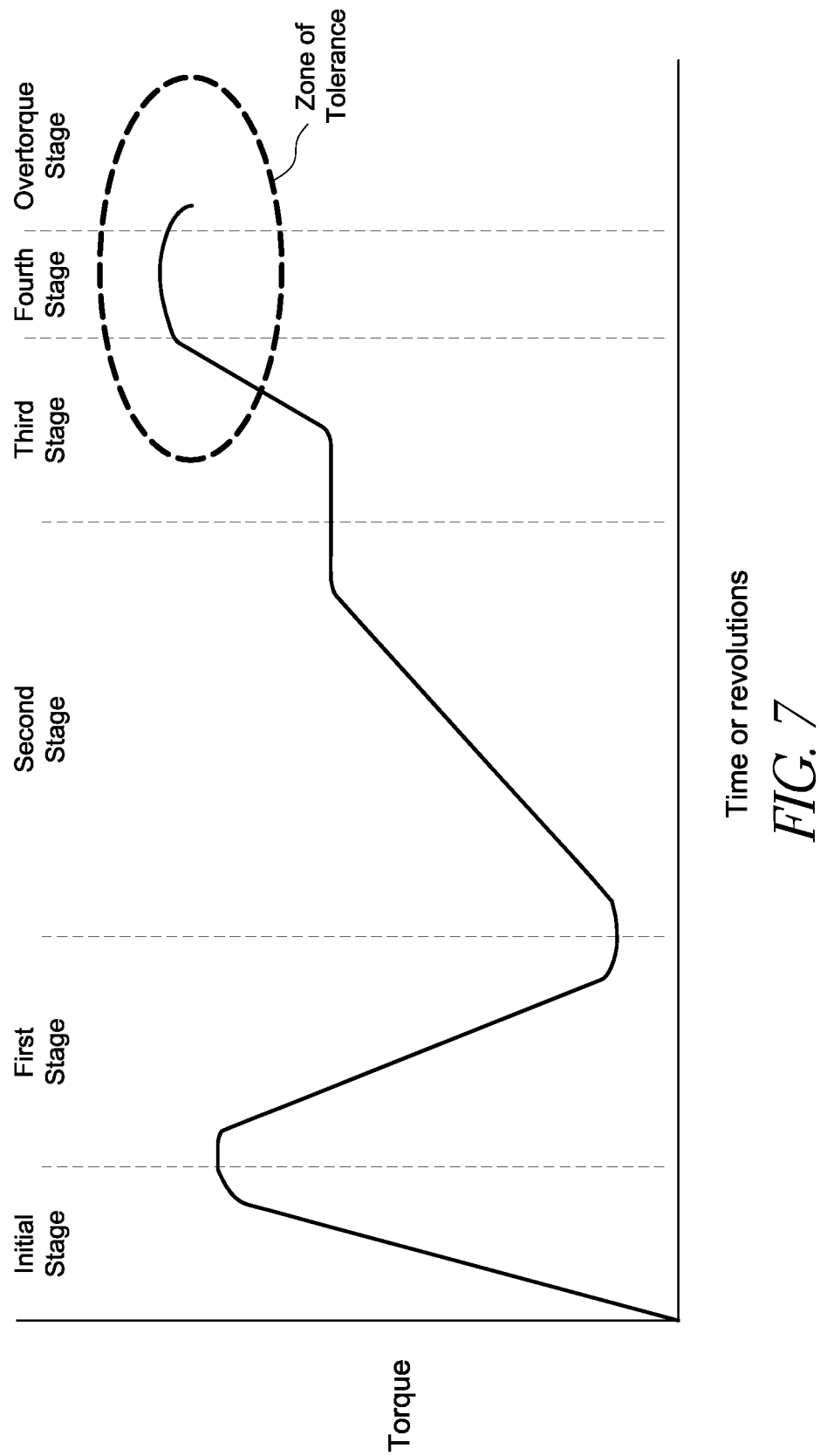
FIG. 7 illustrates a torque plot with a zone of tolerance.
Figure 8:
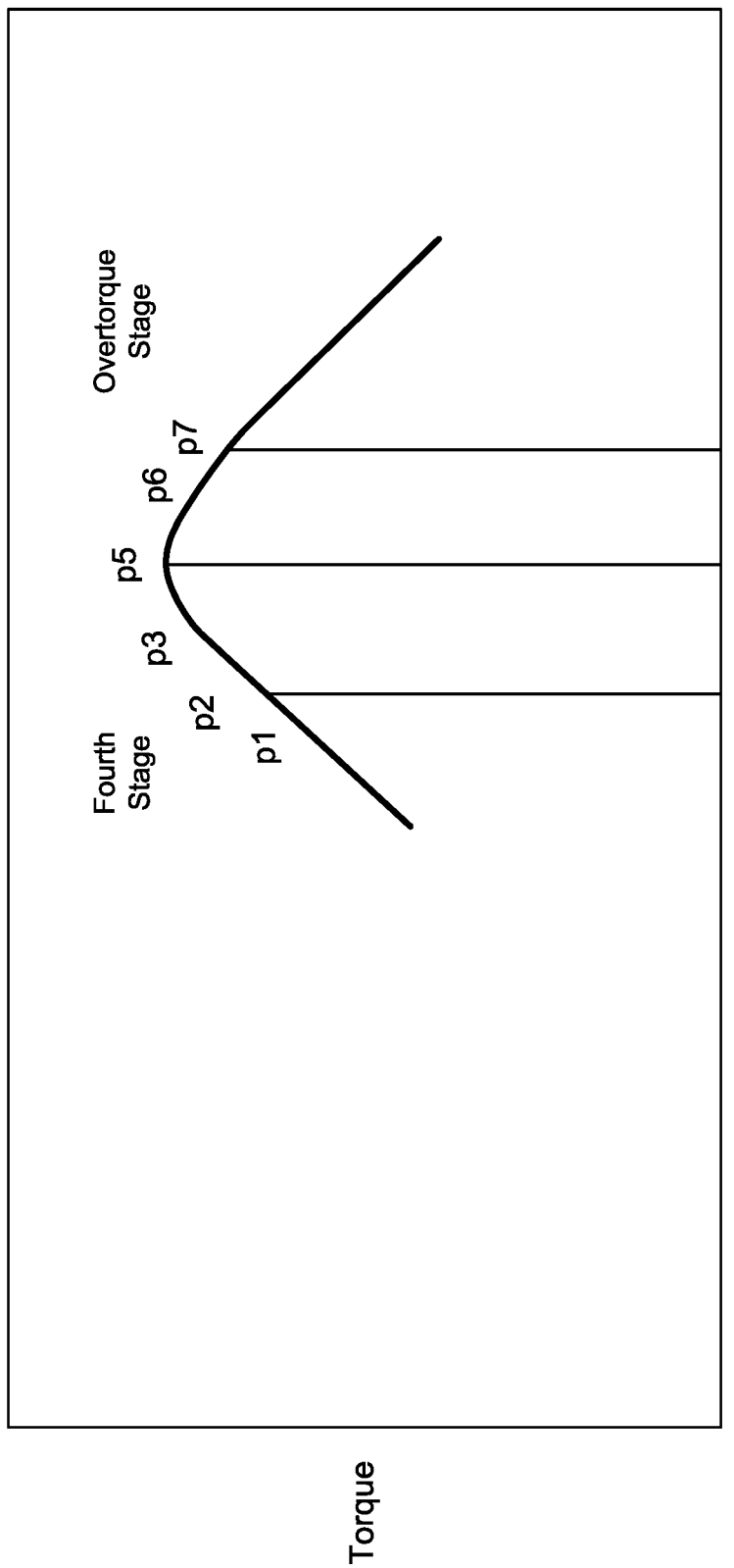
FIG. 8 illustrates a close-up view of an example torque apex.

FIGS. 7 and 8 illustrate a further torque-limiting method and algorithm. As shown, certain embodiments include a "zone of tolerance" prior to and after the apex of the torque curve. Stopping the rotation of the screw in the zone of tolerance can provide confidence that the screw is secured in the bone (e.g., the screw has not been stripped-out).

As shown in FIG. 7, the zone of tolerance can include an inflection point (e.g., the slope changes becomes zero, changes from positive to negative, or otherwise). In some embodiments, the inflection point is in two dimensions, such as torque and time (or revolutions of the screw). Certain implementations of the screwdriver 10 monitor for and/or issue a stop instruction based on the inflection point having been reached. This can enable the screwdriver 10 to stop the motor 12 near, at, or after the inflection point has been reached. In some variants, the motor 12 is partially or completely stopped after the inflection point has been reached and an additional event has occurred. For example, the event can be an amount of torque change (e.g., a torque reduction of at least about: 5%, 10%, 20%, 30%, values between the aforementioned values, or other values), a rotation of the screw occurs (e.g., an additional rotation of at least about: ⅛ turn, ¼ turn, ½ turn, ¾ turn, 1 turn, 2 turns, values between the aforementioned values, or other values), or otherwise.

In some embodiments, the controller 20 determines the zone of tolerance by monitoring the torque for a number of consecutive increasing torque values and a number of consecutive decreasing torque values. For example, the controller 20 can determine when N1 (e.g., 2, 3, 4, 5, 6, 7, etc.) consecutive increasing values have occurred, followed by N2 (e.g., 2, 3, 4, 5, 6, 7, etc.) consecutive decreasing values. This can indicate that the peak has been reached and that the torque-limiting functionality should be engaged. In some embodiments, one or more torque values separate the consecutive increasing values and the consecutive decreasing values. For example, the torque-limiting functionality can be engaged in response to N1 consecutive increasing values can be detected, followed by one or more interim torque values, followed by N2 consecutive decreasing values. This can account for slight variations in the torque at or near the peak and/or for substantially equal peak torque values.

The zone of tolerance can be further seen FIG. 8's close-up view of an example torque apex. As illustrated, the zone of tolerance can include a positive slope portion (also called the upslope portion), a negative slope portion (also called the downslope portion), or both sides of slope. In some embodiments, the torque-limiting algorithm considers both the upslope portion and downslope portion during the screw insertion process. In certain embodiments, the upslope portion of the algorithm facilitates or ensures securing of the screw, while the downslope portion of the algorithm facilitates or ensures that the screwdriver ceases turning the screw after the torque has reached an apex.

Certain embodiments determine the upslope by determining the change in torque over change in time ($\Delta q/\Delta t$) values during the insertion operation. The method can also include measuring X number (e.g., 2, 3, 4, 5, 6, or otherwise) of torque data points. The method can include rotating the screw and monitoring the torque value until the torque value reaches the peak (e.g., apex). For example, the peak can be determined by comparing $\Delta q/\Delta t$ values at different torque sampling points (e.g., 0, 1, 2, 3, 4), such as can be expressed as: $\Delta q(p0)/\Delta t$, $\Delta q(p1)/\Delta t$, $\Delta q(p2)/\Delta t$, $\Delta q(p3)/\Delta t$, $\Delta q(p4)/\Delta t$, etc. In some embodiments, the peak (e.g., when the value of $\Delta q/\Delta t$ has reached its maximum value) indicates that the screw is secured in place and has compressed the bone plate against the bone. If the $\Delta q/\Delta t$ value is at or near zero, then this can indicate that the screw is secured and/or is at or near the peak torque. As such, in certain embodiments, in response to the $\Delta q/\Delta t$ value being at or near zero, screw rotation is stopped (e.g., by stopping the motor 12).

Similarly, certain embodiments determine the downslope by determining the change in torque over change in time ($\Delta q/\Delta t$) values during the insertion operation. However, in using the downslope to determine the peak torque, the $\Delta q/\Delta t$ comparison looks for $\Delta q/\Delta t$ values that are zero or slightly decreasing (e.g., less than about 5% of the previous value) for N number of consecutive points.

Override Functionality

Some embodiments of the screwdriver 10 allow a user to override the torque limitation determined by the controller 20. This can be beneficial (e.g., if the screw happens to stop before seating on the plate) by permitting the user to override the stoppage of the screw. In several embodiments, the screwdriver 10 includes an override input, such as a switch, button, or the like. The override input can be configured to send an override signal to the controller 20, which overrides the controller's stoppage of the screwdriver's turning of the screw.

As noted above, certain embodiments of the override input can facilitate seating the screw against the plate. Sometimes, when placing the screw, the screw head remains "proud" of the bone plate (e.g., a bottom surface of the head of the screw remains spaced apart from a top and/or mating surface of the plate). This can result in a less secure mounting of the plate relative to the bone, can inhibit or prevent healing, and/or can cause the patient discomfort. To aid in remedying a proud screw, or for other reasons, the override input can allow a user to rotate the screw an incremental amount, thereby further driving the screw into the bone and more fully (or completely fully) seating the screw on the plate. In certain implementations, the override input momentarily overrides the torque-limiting feature and allows some or all available power to go to the motor 12 to execute the incremental turn. In various embodiments, activation of the override input provides an additional incremental rotational movement of the screwdriver bit of at least about: 45°, 90°, 135°, 180°, 270°, 360°, 540°, 720°, values between the aforementioned values, or otherwise.

In certain embodiments, the override functionality can be engaged whenever the override input is activated (e.g., depressed). For example, some embodiments allow an override for each activation of the override input and/or do not limit the number overrides permitted. In certain implementations, only a limited number of overrides are allowed. For example, some embodiments only allow one override, after which additional override inputs are ignored. In some embodiments, the override input is configured to rotate the screw a predetermined amount (e.g., 1 revolution, ½ revolution, ¼ revolution, values in between, or otherwise), for each activation of the override input.

According to some variants, activation of the override input allows override operation of the screwdriver 10 for a period of time without requiring additional activation of the override input. This can facilitate convenient operation of other inputs (e.g., controls to drive the screw forward or in reverse) during the override period without the need to repeatedly activate the override input. For example, an override button or other input device can be depressed or otherwise activated to initiate the override time period, during which one or many operations can be performed that would otherwise be inhibited or prevented (e.g., because of the torque-limiting features described above). In some embodiments, the override time period can be at least about: 5 seconds, 10 seconds, 30 seconds, 1 minute, 2 minutes, 5 minutes, values between the aforementioned values, or otherwise.

A variety of override input devices and methods for activating and/or otherwise controlling the override feature are contemplated. For example, in certain embodiments, the override feature is activated by engaging (e.g., pressing and/or holding) a button, or combination of buttons. Some variants include a dedicated button that activates the override feature. Certain embodiments of the override input device include a switch, rocker, slide, proximity sensor, touch screen, or otherwise. Various embodiments can provide feedback (e.g., tactile visual and/or audible) to the user.

Several implementations include an adjustable override input device that can be moved to a plurality of positions to provide different override functionality. For example, the input device can comprise a button, slider, or switch with multiple positions, each with a different override function, such as different operations that are permitted and/or different override time periods.

In some embodiments, the adjustable override input device comprises a wheel or dial that can be rotated between various positions. For example, the wheel or dial can have several (e.g., two, three, four, five, six, or more) positions located a rotational distance apart, such as at least about 45° apart or at least about 90° apart. The screwdriver 10 can be configured to detect the position of the dial or wheel and to provide an incremental rotation of the screwdriver bit or the motor 12 that is about equal to, less than, greater than, or otherwise related to the incremental rotation of the dial or wheel. In certain variants, the incremental rotation of the screwdriver bit is proportional to the rotation of the wheel or dial. In some various embodiments, while rotating the wheel or dial, the user receives tactile or audible feedback, such as distinct "clicks" or detents, such as at each 90° increment.

Certain embodiments have a dial or wheel with multiple positions. For example, the wheel can have three positions that are each located about 90° apart. In some such embodiments, when the dial or wheel is positioned in the first position then the screwdriver 10 will provide a first incremental rotation (e.g., about 90°). When the dial or wheel is positioned in the second position then the screwdriver will provide a second incremental rotation (e.g., about 180°). When the dial or wheel is positioned in the third position then the screwdriver will provide a third incremental rotation (e.g., about 270°).

In some embodiments, the override input device controls the direction of rotation of the bit of the screwdriver 10. This can allow the override input device to control whether the screw is being driven forward or in reverse. In certain variants, the screwdriver 10 drives the screw forward when the override input device is in a first position and reverses the screw when the override input device is in a second position. In some implementations, the override input device is a wheel or dial, and the rotational direction of the screwdriver bit is the same as the direction that the wheel or dial is rotated.

Other Features

Various embodiments of the screwdriver 10 have a variety of operational characteristics. For example, some embodiments provide a maximum rotational speed (at no load) of at least about: 3,000 rpm, 4,000 rpm, 5,000 rpm, 6,000 rpm, 10,000 rpm, values between the aforementioned values, or other values. As noted above, some embodiments slow the rotation of the screw after a slowdown point has been reached. Certain such embodiments have a slowed speed (at no load) of less than or equal to about: 500 rpm, 600 rpm, 700 rpm, 800 rpm, 900 rpm, 1,000 rpm, 1,100 rpm, 1,200 rpm, values between the aforementioned values, or other values. Certain implementations of the screwdriver 10 can provide a torque on the screw of at least about: 25 in-ozs, 30 in-ozs, 35 in-ozs, 40 in-ozs, 45 in-ozs, values between the aforementioned values, or other values. Some embodiments of the screwdriver 10 can provide a torque on the screw of at least about: 25 N-cm, 30 N-cm, 35 N-cm, 40 N-cm, 45 N-cm, values between the aforementioned values, or other values.

The screwdriver 10 can be implemented with various types of motors. In some variants, the motor 12 is powered by a power source, such as a source of AC or DC electrical power. In some embodiments, the motor 12 is powered by an on-board power source, such as a battery, capacitor, or otherwise. In some embodiments, the motor 12 is configured to receive power from an external source, such as from a console, wall socket, or other external power source. In some embodiments, the motor 12 is a brushless DC motor. In some embodiments, the motor 12 is a three-phase electric motor. The motor 12 can include one or more hall sensors, which can send signals to the controller 20 to enable the controller 20 to determine the number of revolutions of the motor 12. In certain variants, the controller 20 determines the number of revolutions of the screw from the number of revolutions of the motor 12.

Some implementations are configured to stop the rotation of the screw by shutting-off (e.g., substantially or totally) the power to the motor 12. Certain implementations include a brake to actively decelerate the motor or components. For example, some implementations include a friction or electromagnetic brake.

Various embodiments of the screwdriver 10 include a forward input that a user can engage to instruct the screwdriver 10 to turn the screw in a forward direction, such as in the direction to insert the screw into the bone. For example, the forward input can be a switch, button, dial, trigger, slider, touchpad, or the like. Certain embodiments have multiple input members, such as a fast forward switch (e.g., the motor will spin at about 4100 RPM at no-load) and a slow forward switch (e.g., motor will spin at 500 RPM at no-load). Some implementations have a reversing input, which can instruct the screwdriver 10 to turn the screw in a reverse direction, such as in the direction to remove the screw from the bone. The reversing input can be similar to the forward input, such as the options described above. In some embodiments, engaging the reversing input causes the motor to spin at about 500 RPM at no-load. In certain implementations, the final rotational speed of the screw is about 500 RPM. In some embodiments, the forward input and the override input are the same component.

In various embodiments, the screwdriver 10 includes components configured to adjust the torque data, such as by filtering the torque data, decreasing noise in a signal from a sensor 18 (e.g., a motor current sensor), or otherwise. For example, the screwdriver 10 can include one or more low-pass filters. The filters can be implemented in hardware and/or software. For example, in some embodiments, the filters comprise resistance capacitor circuitry. Certain embodiments include a software filter configured to filter out certain frequencies and/or levels of torque data. In various embodiments, the filtering components can facilitate a smoother torque curve. In some variants, the filtering components can reduce errors in the torque-limiting functionality that may otherwise be caused by noise and/or outlier measurements.

Summary

Various torque-limiting screwdriver systems and methods have been disclosed in the context of aspects of certain embodiments, examples, and variations. Nevertheless, the present disclosure extends beyond the specifically disclosed embodiments, examples, and variations to other alternative embodiments and/or uses of the invention, as well as obvious modifications and equivalents thereof. In addition, while a number of variations of the screwdriver have been shown and described in detail, other modifications, which are within the scope of this disclosure, will be readily apparent to those of skill in the art based upon this disclosure.

Certain features have been described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Any of the steps and blocks can be adjusted or modified. Other or additional steps can be used. None of the steps or blocks described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

Some of the devices, systems, embodiments, and processes use controllers, which can include a processor and memory. Each of the routines, processes, methods, and algorithms described above may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as volatile or non-volatile storage.

Conditional language used herein, such as, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. The term "and/or" means that "and" applies to some embodiments and "or" applies to some embodiments. Thus, A, B, and/or C is equivalent to A, B, and C written in one sentence and A, B, or C written in another sentence. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Terms relating to circular shapes as used herein, such as diameter or radius, should be understood not to require perfect circular structures, but rather should be applied to any suitable structure with a cross-sectional region that can be measured from side-to-side. Terms relating to shapes, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations. Likewise, shapes modified by the word "generally" (e.g., "generally cylindrical") can include reasonably close approximations of the stated shape.

Some embodiments have been described in connection with the accompanying drawings. The figures are drawn to scale, but such scale should not be limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

In summary, various embodiments and examples of torque-limiting screwdriver systems and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. Moreover, this disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

The following is claimed:

1. A method for controlling a surgical torque-limiting screwdriver comprising a housing; a motor positioned in the housing and configured to receive electrical power from a power source; and a drive head positioned at a distal end of the screwdriver, the drive head configured to receive a bit that engages a screw and to be rotated by the motor so as to enable the screwdriver to drive the screw into a bone; the method comprising:
    determining a plurality of driving torque values, each of the plurality of driving torque values indicative of an amount of torque that the screwdriver is applying to the screw during a respective time period t;
    storing two or more of the most-recent of the plurality of driving torque values in a memory;
    comparing each of the driving torque values that occur after a deadband with a threshold torque value;
    permitting engagement of a torque-limiting function in response to at least one of the driving torque values that occur after the deadband being greater than or equal to the threshold torque value;
    reducing the rotational speed at which the screwdriver drives the screw in response to at least one of the driving torque values that occur after the deadband being greater than or equal to the threshold torque value; and
    engaging the torque-limiting function in response to determining that at least a threshold number of the driving torque values that occur after the deadband consecutively decrease, wherein engaging the torque-limiting function stops the driving of the screw by the screwdriver, and wherein the method is performed by a controller of the screwdriver.

2. The method of claim 1, wherein the deadband is an amount of rotations of the screw.

3. The method of claim 1, wherein the time period t is approximately 10 ms.

4. The method of claim 1, wherein reducing the rotational speed comprises reducing it to less than or equal to 900 rpm.

5. The method of claim 1, wherein reducing the rotational speed comprises reducing it by a factor of approximately 4.

6. The method of claim 1, wherein the threshold torque value is at least 15 N-cm.

7. The method of claim 1, wherein the threshold number is two or more.

8. A method for controlling a surgical torque-limiting screwdriver comprising:
rotating a screw with the surgical torque-limiting screwdriver, thereby driving the screw into bone;
determining a plurality of torque values at a corresponding plurality of times;
in response to determining that fewer than a threshold number of the plurality of torque values consecutively decrease, determining one or more subsequent torque values; and
in response to determining that at least the threshold number of the plurality of torque values consecutively decrease, activating a torque-limiting function;
wherein activating the torque-limiting function comprises stopping the rotating of the screw by the screwdriver, and
wherein the method is performed by a controller of the screwdriver.

9. The method of claim 8, wherein the threshold number is two or more.

10. The method of claim 8, wherein the threshold number is between 2 and 20.

11. The method of claim 8, further comprising storing at least the most-recent threshold number of determined torque values in a memory.

12. The method of claim 8, wherein determining the plurality of torque values at a corresponding plurality of times comprises detecting a plurality of currents being drawn from a motor of the screwdriver.

13. The method of claim 8, wherein the determined plurality of torque values comprises a determined plurality of torque arrays, wherein each array is an average of two or more consecutive torque values over a period of time, each period of time comprising two or more time increments.

14. A method for controlling a surgical torque-limiting screwdriver comprising:
rotating a screw with the surgical torque-limiting screwdriver, thereby driving the screw into bone;
determining a plurality of consecutive torque values at a corresponding plurality of consecutive times; and
in response to determining that at least a threshold number of the plurality of consecutive torque values consecutively decrease, activating a torque-limiting function.

15. The method of claim 14, further comprising in response to determining that fewer than the threshold number of the plurality of consecutive torque values consecutively decrease, continue determining one or more subsequent torque values until the threshold number is reached.

16. The method of claim 14, wherein activating the torque-limiting function comprises stopping the rotating of the screw by the screwdriver.

17. The method of claim 14, wherein the threshold number is two or more.

18. The method of claim 14, wherein the threshold number is between 2 and 10.

19. The method of claim 14, further comprising storing at least the most-recent threshold number of determined consecutive torque values in a memory.

20. The method of claim 14, wherein determining the plurality of torque values at a corresponding plurality of times comprises detecting a plurality of currents being drawn from a motor of the screwdriver.

21. The method of claim 14, wherein the determined plurality of consecutive torque values comprises a determined plurality of consecutive torque matrices, wherein each matrix is an average of two or more consecutive torque values over a period of time.

22. The method of claim 14, wherein the method is performed by a controller of the screwdriver.

* * * * *